(12) United States Patent
Yan et al.

(10) Patent No.: US 7,714,996 B2
(45) Date of Patent: May 11, 2010

(54) AUTOMATIC INSPECTION SYSTEM FOR FLAT PANEL SUBSTRATE

(75) Inventors: Zheng Yan, Sunnyvale, CA (US); Bo Li, Sunnyvale, CA (US); Wayne Chen, Sunnyvale, CA (US); Tony Young, Sunnyvale, CA (US); Ning Li, Sunnyvale, CA (US); Jianbo Gao, Sunnyvale, CA (US)

(73) Assignee: 3i Systems Corporation, Santa Clara, CA (US)

( * ) Notice: Subject to any disclaimer, the term of this patent is extended or adjusted under 35 U.S.C. 154(b) by 302 days.

(21) Appl. No.: 11/714,513

(22) Filed: Mar. 5, 2007

(65) Prior Publication Data
US 2008/0174771 A1 Jul. 24, 2008

Related U.S. Application Data

(63) Continuation-in-part of application No. 11/626,102, filed on Jan. 23, 2007, now Pat. No. 7,564,544.

(51) Int. Cl.
*G01N 21/00* (2006.01)
(52) U.S. Cl. .............................. 356/237.1; 356/237.5
(58) Field of Classification Search ... 356/237.1–237.5, 356/455–448, 601–623
See application file for complete search history.

(56) References Cited

U.S. PATENT DOCUMENTS

| | | | | |
|---|---|---|---|---|
| 5,883,714 A * | 3/1999 | Jann et al. | ..................... | 356/484 |
| 6,714,283 B2 * | 3/2004 | Laurent et al. | ............. | 356/3.07 |
| 7,410,793 B2 * | 8/2008 | Boege et al. | ............. | 435/288.7 |
| 7,420,691 B2 * | 9/2008 | Fukui | ......................... | 356/632 |
| 2005/0052643 A1 * | 3/2005 | Lange et al. | ............. | 356/237.1 |
| 2005/0122509 A1 * | 6/2005 | Backhauss | ............... | 356/237.2 |

* cited by examiner

*Primary Examiner*—Hoa Q Pham
(74) *Attorney, Agent, or Firm*—Courtney Staniford & Gregory LLP

(57) ABSTRACT

Automatic optical inspection (AOI) systems are described comprising optical modules that include an illumination component and a lens array configured to direct illumination of the illumination component at a portion of a substrate. The lens array includes a Fresnel lens. The optical module includes a camera that receives reflected light resulting from an interaction of the illumination and the substrate. The camera includes a time delay integration (TDI) sensor. A telecentric imaging lens directs reflected light from the substrate to the camera. The illumination component comprises a controller coupled to multiple LED light sources, each emitting light at a different wavelength. The controller independently controls each LED light source. The illumination component includes a bright field and/or a dark field light source. The illumination component can include a front side and/or a back side light source. An optical fiber is coupled to the camera and an image processor.

44 Claims, 13 Drawing Sheets

AUTOMATIC INSPECTION SYSTEM FOR FLAT PANEL SUBSTRATE

RELATED APPLICATION

This application is a continuation-in-part application of U.S. patent application Ser. No. 11/626,102, filed Jan. 23, 2007 now U.S. Pat. No. 7,564,544.

TECHNICAL FIELD

The disclosure herein relates generally to inspection systems and, in particular, to systems and methods for inspecting and detecting defects in printed patterns on flat substrates.

BACKGROUND

Defect monitoring and control are critically important in the manufacturing and production of large substrates like for example the substrates used in flat panel displays (FPDs). The FPDs are flat panel display screens used for portable personal computers (PCs), flat desktop monitors, mobile phones and digital devices, car navigation systems, video cameras, projection and the recently introduced flat and thin LCD televisions, and many other large and small display screens on various devices and appliances. The FPDs include, for example, Thin Film Transistor-Liquid Crystal Display (TFT-LCD) substrates. A typical LCD consists of two transparent substrates (typically glass) with control circuitry (TFT) and optical filters printed on their surfaces and filled with liquid crystal material between the two substrates. The FPD manufacturing process is complex and carried out in a highly sterile environment. Production of FPDs is susceptible to various defects introduced during the fabrication process, which may force the manufacturer to discard or repair panels. Hence the production yield suffers and product cost increases. Therefore, detection of defects in the substrates is critical to the manufacturer's success.

There are many types of defects in the TFT manufacturing process, including, but not limited to, fall-ons (particles of foreign material that fell on the glass during manufacturing), opens and shorts (a trace that became open and separate traces that became connected, respectively), chemical residues (puddles of chemicals left on the surface), and pinholes (through holes that create shorts between layers). These defects can result in deficiencies from dead pixels to malfunctioning panels.

Substrate inspection during steps of the manufacturing process facilitates quality control and process control, and helps minimize material loss resulting from those manufacturing defects. The inspection of FPDs presents special technological challenges because of the transparent materials used, multi-layer structure, high-density features, fine nature of potential defects (measured in single microns), large substrate area, and tact time (i.e., throughput) requirements. Automatic optical inspection (AOI) is used in the manufacturing processes of TFT-LCDs and semiconductor integrated circuit (IC) chips to diagnose the quality of manufactured components and improve the yield of the production, thus reducing manufacturing costs.

Conventional AOI systems use a camera to generate an image of the substrate. The resulting image is analyzed in an attempt to detect defects in the substrate. Analysis of the image provides information of defects, where the defect information includes one or more of location (e.g., x-coordinate position, y-coordinate position, data, gate, zone, etc.), size, and type of the defect. Additionally, the analysis provides information of trends in the number of defects as well as the defect type and location. The information of the analysis helps manufacturers optimize their yield management.

The fundamental performance of AOI is measured predominantly using the key specifications of speed and sensitivity of inspection. The advances in manufacturing technology have lead to higher speeds of fabrication, substrates having increasingly larger sizes, and printed patterns (on substrates) having ever smaller dimensions, all of which result in a more demanding need for AOI with higher speed and better sensitivity. Consequently, there is a need for AOI systems and methods that provide relatively high-speed analysis of large panel substrates (e.g., LCD glass substrates, semiconductor wafers, etc.) while delivering high resolution images and providing higher levels of sensitivity in defect detection.

INCORPORATION BY REFERENCE

Each publication, patent, and/or patent application mentioned in this specification is herein incorporated by reference in its entirety to the same extent as if each individual publication and/or patent application was specifically and individually indicated to be incorporated by reference.

DETAILED DESCRIPTION

Automatic optical inspection (AOI) systems and methods are described below for use in inspecting, identifying and characterizing defects in printed patterns on FPD substrates such as LCDs, organic light emitting diode (OLED) substrates, masks and semiconductor wafers during manufacturing processes. The AOI systems and methods, collectively referred to herein as "AOI systems," comprise optical modules that include an illumination component and a lens array configured to direct illumination of the illumination component at a portion of a substrate. The lens array includes at least one Fresnel lens. The optical module includes a camera positioned to receive reflected, scattered or transmitted light resulting from interactions of the illumination with the substrate. The camera includes a time delay integration (TDI) or line scan charge-coupled device (CCD) sensor. A telecentric imaging lens directs the reflected, scattered or transmitted light from the substrate to the camera.

The illumination component comprises a controller coupled to multiple LED light sources, and each LED light source emits light at a different wavelength. The controller is configured to independently control each of the LED light sources. The illumination component can include front side light sources, which include a bright field light source and/or a dark field light source, and/or a back side light source. Alternative embodiments of the AOI systems described herein can include a single LED source emitting light having different wavelengths. A feedback system is coupled to an output of the camera, and the feedback system controls the illumination component, and/or a gain of the camera. An electrical or fiber optic cable links the camera to an image acquisition and processing unit.

In the following description, numerous specific details are introduced to provide a thorough understanding of, and enabling description for, embodiments of the inspection systems and methods. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

Figure 1:
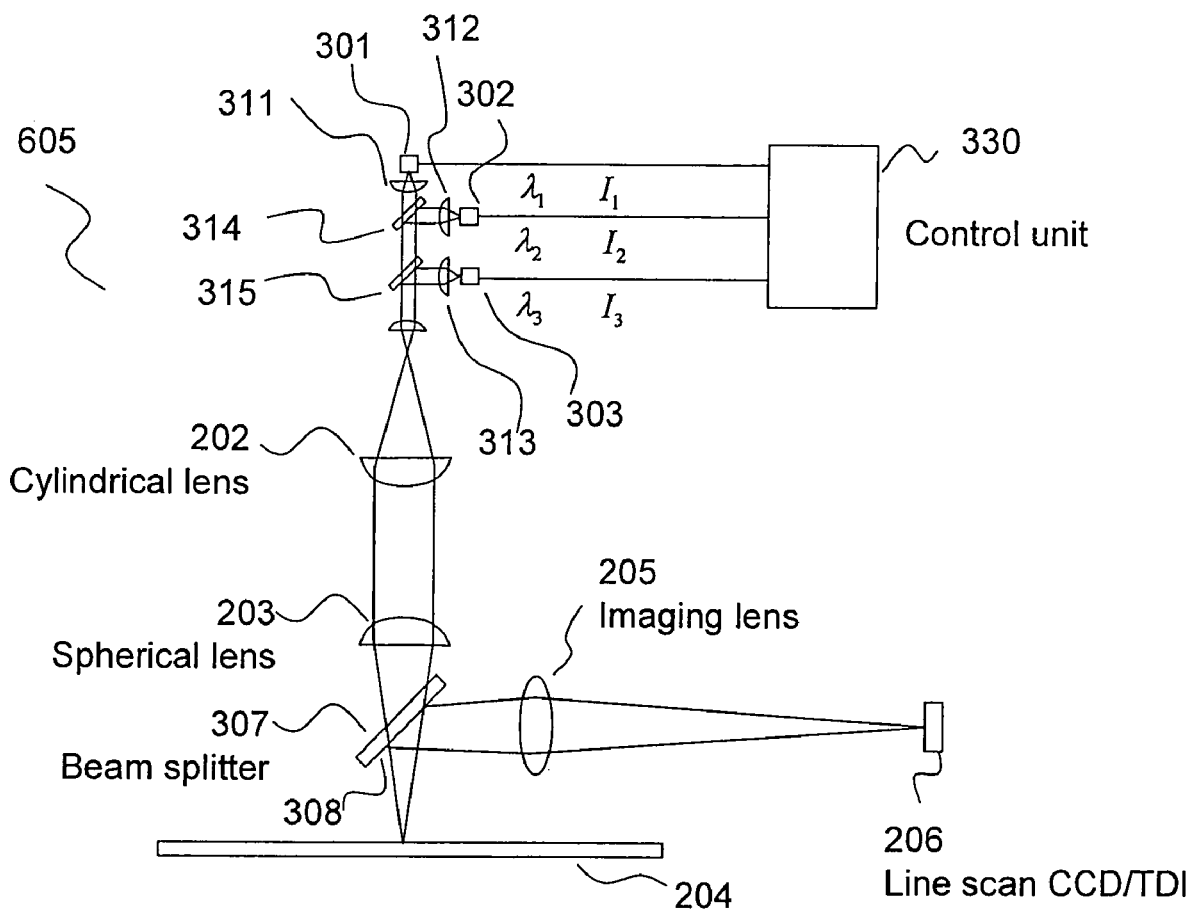
FIG. 1 is a block diagram of an optical module of an automatic optical inspection (AOI) system, under an embodiment.

FIG. 1 is a block diagram of an optical module 605 of an automatic optical inspection (AOI) system, under an embodiment. The optical module 605 is configured to inspect a substrate as well as identify and locate defects on or in the substrate by providing a defect signal that is proportional to the product of light power illuminating the substrate and integration time. The optical module 605 includes multiple LED light sources, where each of the LED light sources is configured to provide light at a different wavelength for inspecting a flat surface. Though three LEDs at three different wavelengths are shown in this example optical module 605, other numbers of LEDs and/or wavelengths may be used. The multiple light sources of the optical module 605 include LED 301 generating light at wavelength $\lambda_1$, LED 302 generating light at wavelength $\lambda_2$, and LED 303 generating light at wavelength $\lambda_3$. The output light beams of the LEDs are collimated by lenses 311, 312, and 313, and combined by dichroic beam splitters 314 and 315. The dichroic beam splitter 314 reflects the light at wavelength $\lambda_2$ and transmits the light at wavelength $\lambda_1$. The dichroic beam splitter 315 transmits the light at wavelengths $\lambda_1$ and $\lambda_2$, and reflects the light at wavelength $\lambda_3$.

A control unit 330 independently controls the intensities of the light at the three wavelengths. The light intensity I illuminating the sample surface is given by an equation $$I=I_1+I_2+I_3$$

where $I_1$, $I_2$, and $I_3$ are the output intensity of LED light sources at wavelengths of $\lambda_1$, $\lambda_2$, and $\lambda_3$, respectively. The light intensities $I_1$, $I_2$, and $I_3$ of the LED light sources 301-303 are individually adjustable from 0 to 100% of the total light intensity to optimize for defect detection sensitivity on different sample surfaces. For example, both the optical properties and thickness of a thin film coating on a substrate affect the reflectivity differently at different wavelength, and, as a result, some wavelengths have better defect detection sensitivity than other wavelengths. The adjustable combination of the relative intensities of different wavelengths allows optimization of defect detection sensitivity, which is very difficult to implement with a conventional fiber line light.

In addition, the continuously adjustable relative weights of each wavelength enable the optical module 605 to compensate for the non-uniform spectral transmission of the optical system and the non-uniform spectral response of the CCD sensor. As a result, the optical module 605 provides a true flat illumination spectrum, which is desirable in inspecting the surface that has higher noise induced by film thickness variations. Dark field illumination and imaging (not shown) can also be implemented by adding another light source, for example a laser, to illuminate the surface at an angle from the normal to the surface.

The optical module 605 includes a cylindrical lens 202 and a spherical lens 203 in the illumination path between the dichroic beam splitter 315 and a beam splitter 307. The cylindrical lens 202 and the spherical lens 203 are configured and/or positioned to shape the output of the discrete LED light. The illuminated area is a narrow line focused on the substrate surface. The area should be optimized to match one or more of the aspect ratio, size and location of the field of view (FOV) of the imaging sensor on the substrate. The optical module 605 includes an imaging lens 205 positioned in the reflection path of the beam splitter 307, and the beam splitter 307 is oriented so that the beam splitting surface 308 is directed towards the imaging lens 205 so that the light ray from the surface 204 of the sample or substrate does not pass through the beam splitter 307. In this manner the AOI system 605 of an embodiment eliminates any aberrations induced by the thickness of the beam splitter. Light from the imaging lens 205 is directed at a line scan charge-coupled device (CCD)/time delay integration (TDI) (CCD/TDI) camera 206, as described below.

Figure 2:
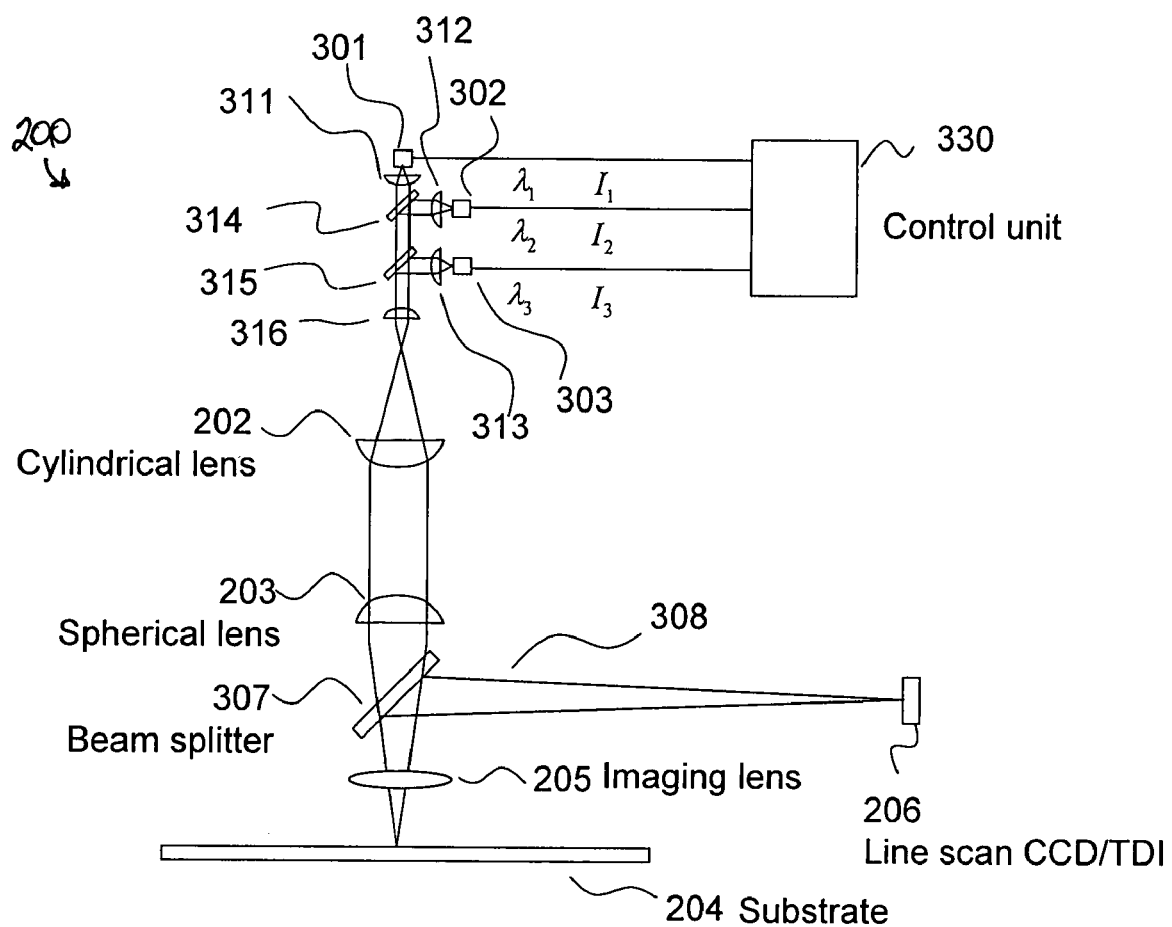
FIG. 2 is a block diagram of an optical module of an AOI system, under an alternative embodiment.

FIG. 2 is a block diagram of an optical module 200 of an AOI system, under an alternative embodiment. The AOI system 200 includes multiple LED light sources, where each of the LED light sources is configured to provide light at different wavelengths. Though three LEDs at three different wavelengths are shown in this example optical module 200, alternative embodiments can include varying numbers of LEDs and/or wavelengths. The multiple light sources of the optical module 200 include LED 301 generating light at wavelength $\lambda_1$, LED 302 generating light at wavelength $\lambda_2$, and LED 303 generating light at wavelength $\lambda_3$. The output lights of the LEDs are collimated by lenses 311, 312, and 313, and combined by dichroic beam splitters 314 and 315. The dichroic beam splitter 314 reflects the light at wavelength $\lambda_2$ and transmits the light at wavelength $\lambda_1$. The dichroic beam splitter 315 transmits the light at wavelengths $\lambda_1$ and $\lambda_2$, and reflects the light at wavelength $\lambda_3$.

A control unit 330 independently controls the intensities of the light sources at the three wavelengths. The light intensity I illuminating the sample surface is as described above with reference to FIG. 1. The intensities $I_1$, $I_2$, and $I_3$ of the LED light sources 301-303 are independently adjustable from 0 to 100% of the total light intensity to optimize for defect detection sensitivity on different sample surfaces.

The optical module 200 includes a cylindrical lens 202 and a spherical lens 203 in the illumination path between the dichroic beam splitter 315 and beam splitter 307. The cylindrical lens 202 and the spherical lens 203 are configured and/or positioned to shape the output of the discrete LED light. The illuminated area is a narrow line focused on the substrate surface. The area of an embodiment is optimized to match the aspect ratio of the imaging sensor. The optical module 200 includes an imaging lens 205 positioned in the light path between the beam splitter 307 and the substrate surface 204. The beam splitter 307 is oriented so that the beam splitting surface directs reflected light 308 from the substrate surface towards a CCD/TDI camera 206.

The optical module 200 includes lenses 311, 312, 313, 316, 202 and 203 in the light path between the light sources and the beam splitter 307. Each of lenses 311, 312, 313, 316, 202 and 203 are configured to collect and direct light from the light sources 301-303 to the substrate surface 204, and each of the lenses 311, 312, 313, 316, 202 and 203 comprise a Fresnel lens.

Figure 3:
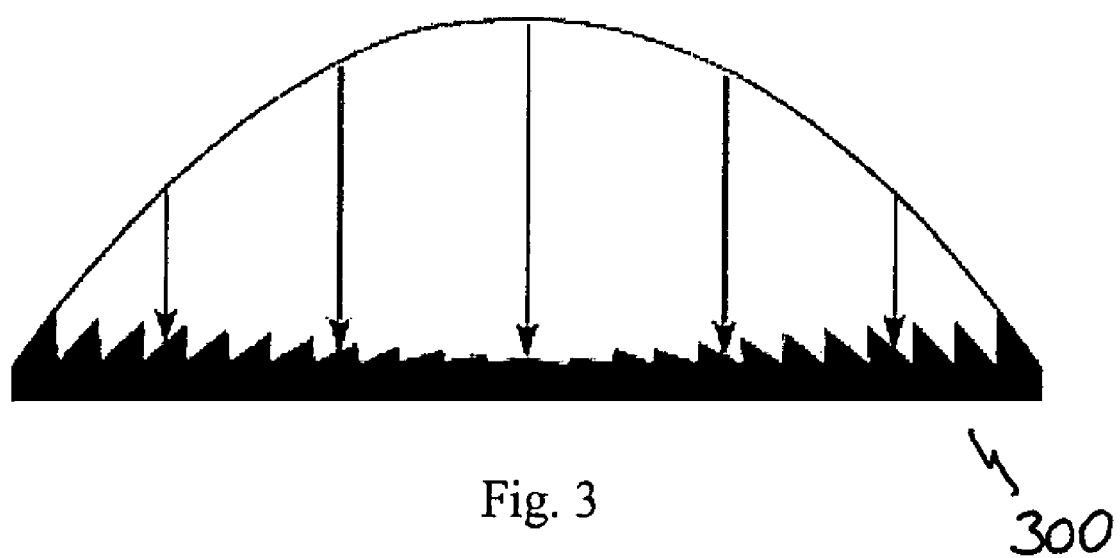
FIG. 3 shows an example Fresnel lens of an AOI system optical module, under an embodiment.

FIG. 3 shows an example Fresnel lens 300 of the optical module 200, under an embodiment. The optical module 200 uses an acrylic Fresnel lens 300 to replace conventional lens in the illumination path. The Fresnel lens 300 replaces the bulk of material of a conventional lens with a series of grooves, molded into the surface of a thin, light-weight plastic sheet. The Fresnel lens 300 provides a lens having a large aperture and short focal length without the weight and volume of material which would be required in other lenses. Compared to other lenses types, the Fresnel lens 300 is much thinner, thus passing more light. Because the Fresnel lens is thin, little or no light is lost by absorption. The Fresnel lens 300 reduces the amount of material required compared to a conventional spherical lens by breaking the lens into a set of concentric annular sections known as Fresnel zones. For each of the Fresnel zones, the overall thickness of the lens is decreased, effectively chopping the continuous surface of a standard lens into a set of surfaces of the same curvature, with discontinuities between them. This allows a substantial reduction in thickness (and thus weight and volume of material) of the lens, at the expense of reduced imaging quality of the lens. The configuration of the optical module 200 enables use of the Fresnel lens 300 because the TDI sensor acquires a single pixel each time in the scan direction, not an image, and because the illumination line in the optical module 200 is much wider than the width of the imaging field, so only a small, relatively uniform portion of the line formed on the surface is used. Therefore, any reduced imaging quality of the Fresnel lens does not prevent it from being used in the AOI system illumination.

The reflected light 308 from the substrate 204 is required to be perpendicular to the TDI camera 206 sensor because the direction the image is moving in the same direction as the charge is moving (through the detectors of the camera 206). Referring to FIG. 1, some optical module configurations meet this requirement by passing incident light through the beam splitter 307 to illuminate the substrate surface 204. The same beam splitter is used to direct reflected scattered and/or transmitted light 308 from the substrate 204 towards the TDI camera 206. Imaging lens 205 is positioned in the light path to image light from the substrate surface 204 onto the TDI camera 206 sensor.

The optical module 200 of an embodiment uses a relatively more compact configuration that positions the imaging lens 205 between the beam splitter 307 and the substrate surface 204 so that the imaging lens 205 is used to direct light at and collect reflected light from the substrate surface 204. The imaging lens 205 in the optical module 200 has a relatively small working distance. When the magnification is fixed in the optical module 200, the distance between imaging lens 205 and TDI camera 206 is also reduced.

For the reasons described above, the optical module 200 includes an imaging lens 205 that is a telecentric lens. Generally, the telecentric lens is configured so that the reflected light from all points across an object or image are collimated. A telecentric lens is a compound lens with an unusual property of providing coaxial light comprising image-forming rays. The AOI of an embodiment uses a telecentric lens because the resulting images have constant magnification and geometry, and this provides for determination of the precise size of objects independently from their position within the field of view (FOV) and even when their distance is affected by some degree of unknown variations. The use of the telecentric lens in combination with the LED light sources of an embodiment optimizes the telecentric effect because the LEDs are telecentric illuminators that produce a parallel light flow. Thus, the light incident on and the light reflected from the substrate surface 204 have the same optical path through the image lens 205.

In contrast to conventional lenses, telecentric lenses have the same magnification at all distances of the object from the camera resulting in the telecentric lens creating images of the same size for objects at any distance and with a constant angle of view across the entire field of view. An object that is too close or too far from the telecentric lens may still be out of focus, but the resulting blurry image will be the same size as the correctly-focused image would be.

The telecentric lens as used in the machine vision system of an embodiment thus provides dimensional and geometric invariance of images within a range of different distances from the lens and across the entire field of view. Use of telecentric lens in the AOI machine vision system of an embodiment therefore overcomes the issues associated with use of conventional lenses in machine vision applications, issues including, but not limited to, changes to the apparent size of objects with varying distance from the camera, and variance in the apparent shape of objects with distance from the center of the FOV (objects appearing close to the edges are viewed with a conventional lens from an angle, while objects near the center of the FOV are viewed frontally).

A substrate under inspection generally has two surfaces including a lower surface that is the substrate and an upper surface or coating that has a pattern structure. The telecentric lens does not receive shadow images from other reflecting surfaces beneath the surface of interest (i.e., the upper surface) because the shadow is right below the pattern when the illumination light is normal incident on the substrate. The image taken by TDI is the top view of the substrate. All the shadows of the lower surface are blocked by the patterns above them. The shadow image acts as the background noise in the imaging process. Thus, the use of telecentric imaging lens reduces background noise of the AOI system 200.

The optical module 200 of an embodiment includes a TDI camera 206 to capture images of the substrate as described above. The TDI camera is a line scan camera that includes a TDI sensor. The TDI camera generally accumulates multiple exposures of the same object and, in effective, increases the integration time available to collect incident light. The object undergoing imaging is in motion, and the motion is synchronized with the TDI camera exposures to ensure a crisp image.

The TDI camera allows for capturing large amount of signal in a relatively short sample time, and thereby provides line scanning that has an increased response compared to other video scanning methods. As such, the TDI camera permits relatively higher scanning speeds in low light, or allows reduced lighting levels (and costs) at conventional speeds.

The TDI camera sensor includes multiple rows of photo-detectors or sensors (e.g., from four (4) to 96 rows of photo-detectors). Each photodetector in a row of photodetectors collects a charge proportional to the number of photons that strike the photodetector. The TDI camera-based system is based on the time-delayed multiple exposure of a moving object, so the AOI system moves the substrate to be inspected in synchronization with the acquisition of line images by the TDI camera. The movement allows the substrate to pass through the field of view of the TDI camera one line at a time in the same way a document passes through a scanner.

As the substrate moves past the TDI camera, the acquired line image of a portion of the substrate shifts from one row of detectors to the next. Simultaneously, the TDI camera's electronics move the stored electrons so they match the movement of the image. Therefore, as the substrate moves past the TDI camera the charges representing the substrate image are shifted to an adjacent row of photodetectors in the TDI sensor and are accumulated. In this way, the TDI sensor integrates the image of each line over several rows of sensors, thus gathering more light per exposure. The TDI camera sends the line image information to a frame-grabber board, for example, which assembles the pixel information into a complete image.

The integrated image signals benefit from increased signal-to-noise ratio and increased dynamic range. With more effective integration time, an increase can be realized in the speed of movement of the target object. Further, because TDI camera operation effectively averages out fluctuations in light intensity to represent a DC light source, the TDI camera enables the use of LED light sources instead of high-powered, high-cost, high-temperature halogen lighting with DC power, thereby lowering system maintenance costs. While the AOI system of an embodiment uses a TDI camera 206, other high sensitivity detectors such as intensified CCD (ICCD), photomultiplier tube (PMT) array, line scan CCD, complementary metal-oxide-semiconductor (CMOS) detector are within the scope of the AOI system 200.

The AOI systems described above use bright field detection methods for substrate inspection. The bright field methods derive the substrate surface image directly from reflected light of the surface. However, some defects (e.g., scratch, particle, etc.) have strong dark field optical information, while others have strong bright field optical information. Therefore, to reliably detect a large range of defects, the AOI system of an alternative embodiment uses dark field methods in addition to the bright field methods to inspect the substrate.

Figure 4:
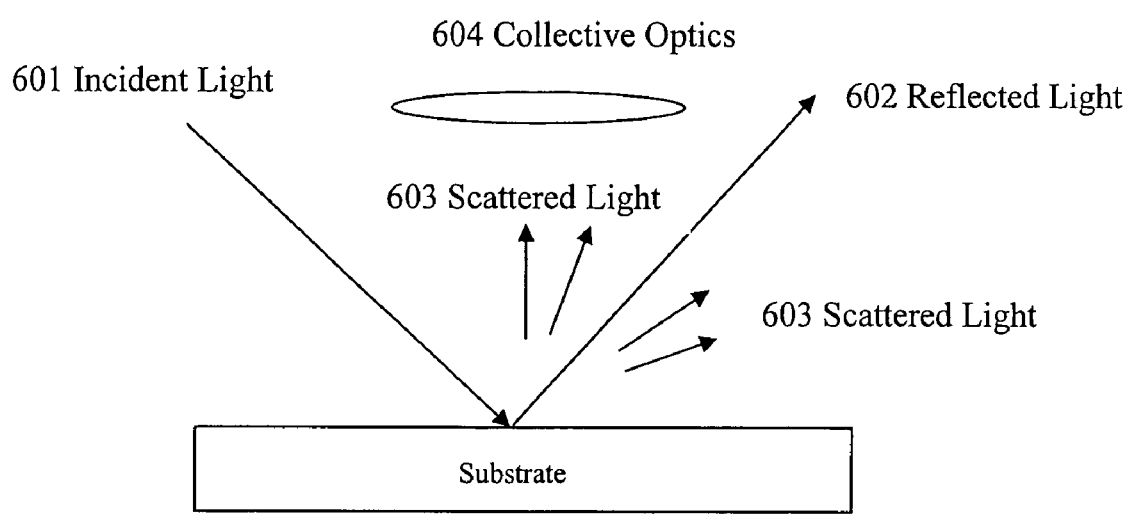
FIG. 4 shows the use of a dark field inspection method in the AOI system, under an embodiment.

FIG. 4 shows the use of a dark field inspection method in the AOI system, under an embodiment. The dark field method directs incident light 601 at the substrate from one or more off-angle positions. Reflected light 602 and scattered light 603 result from interaction of the incident light 601 with the substrate. The collective optics (lens) 604 collect the scattered light 603 from the substrate surface and direct the scattered light 603 to a detector.

Figure 5:
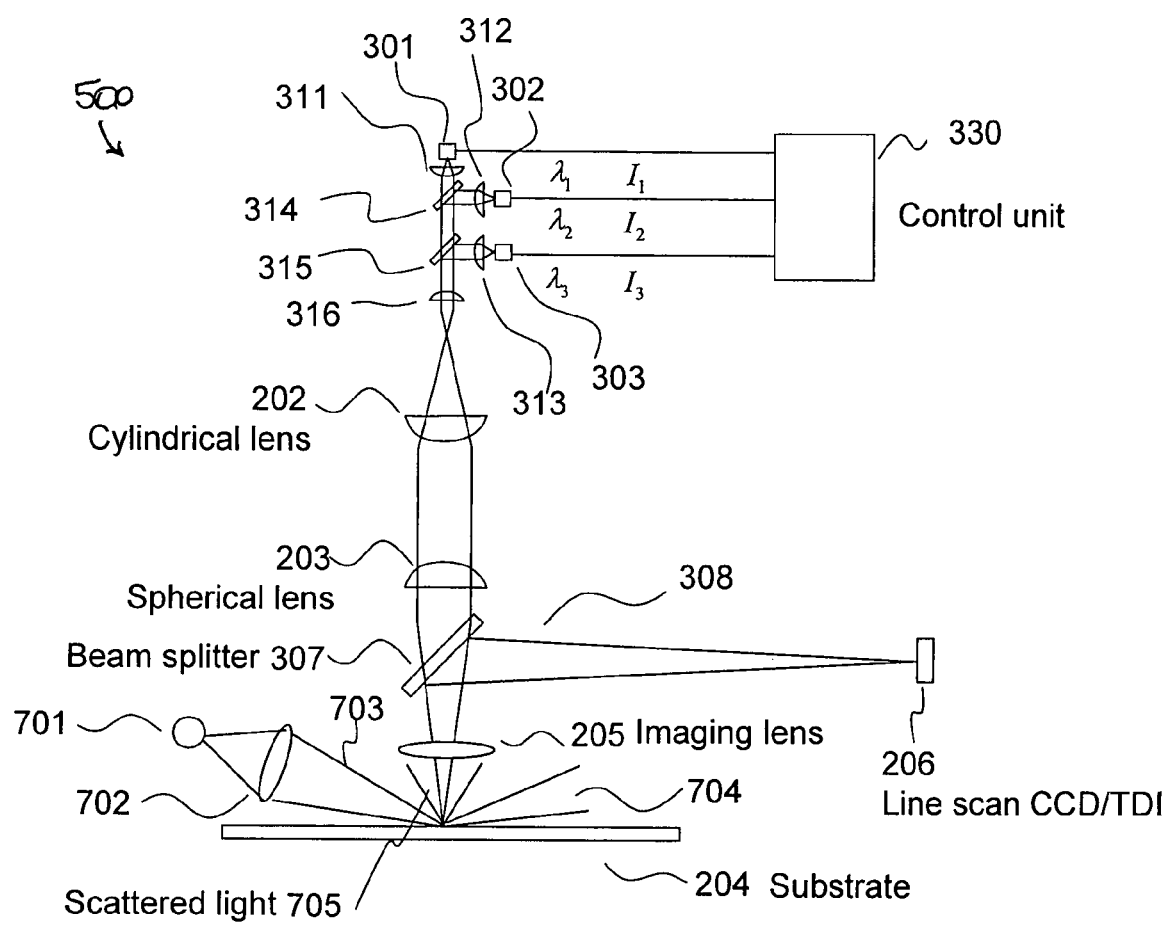
FIG. 5 is a block diagram of an AOI system optical module using bright field and dark field inspection, under an embodiment.

FIG. 5 is a block diagram of an AOI system optical module 500 using bright field and dark field inspection, under an embodiment. The bright field inspection of the optical module 500 is configured and functions as described above with reference to FIG. 3 (optical module 300). The optical module 500 includes a dark field light source 701 in addition to the bright field LED sources 301-303 described above. The dark field light source 701 includes one or more of an LED, lamp, fiber illuminator, and laser source to name a few. Lens 702 focuses incident light 703 from dark field light source 701 to the substrate surface 204. The dark field illumination area overlaps with the bright field illumination area. The interaction of the incident light 703 with the substrate surface 204 produces reflected light 704 and scattered light 705. Imaging lens 205 collects the scattered light 705 and forms an image on a sensor of the TDI camera 206.

The AOI system of an embodiment uses backlighting or back side illumination to image the substrate. Backlighting is configured to position the illuminator under the substrate being imaged. The backlighting provides high contrast for some defects (e.g., islands on glass substrate). When the inspection sample is a glass substrate, for example, backside illumination can detect surface defects as well as internal defects.

Figure 6:
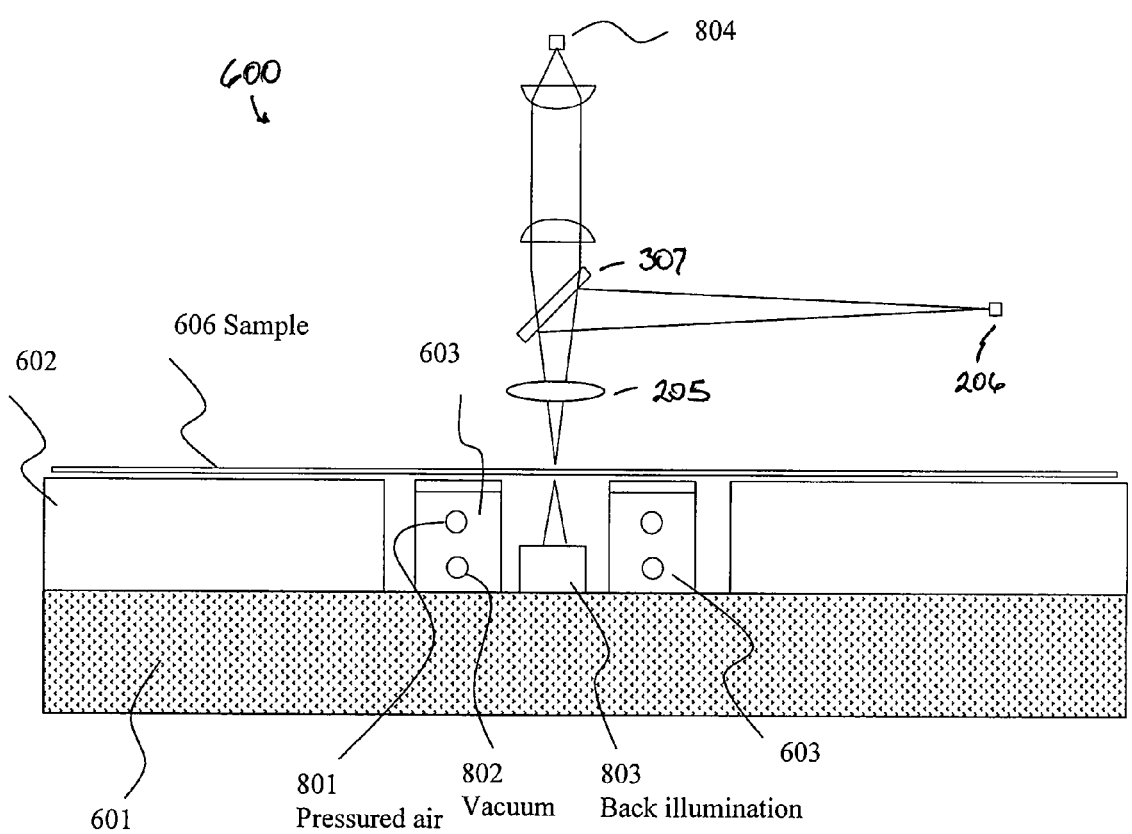
FIG. 6 is a block diagram of an AOI system optical module using backlighting, under an embodiment.

FIG. 6 is a block diagram of an AOI system optical module 600 using backlighting, under an embodiment. The backlighting enhances detection of defects that are otherwise difficult to detect with front side lighting. The AOI system 600 includes a front side light source 804 and a back side light source 803. The front side light source 804 can include light sources as described above. The back side light source 804 can be one or more of an LED, lamp, and fiber optic illuminator. The numerical aperture (NA) of the back side light source 803 matches that of the front side light source 804 in order for most of the light to reach the TDI camera. Both light sources illuminate the same area of the substrate surface. The optical module 600 includes two vacuum preload air bearing chucks 603, and a region between the chucks 603 contains the backside light source 803. The chucks include a pressure air input 801 and a vacuum outlet 802, where the vacuum provides a down force to stabilize the substrate during high-speed motion on an air bearing conveyer, for example.

Figure 7:
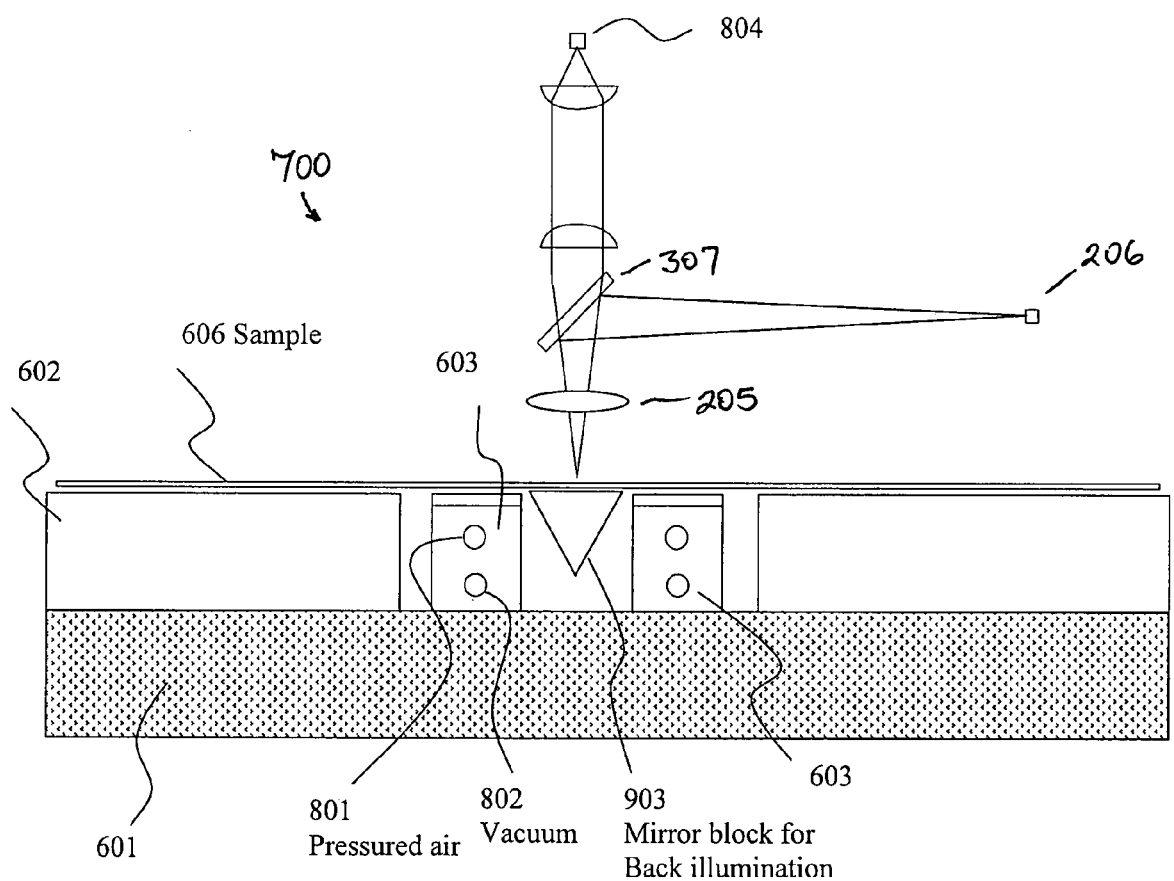
FIG. 7 is a block diagram of an AOI system optical module that includes a mirror for backside illumination, under an embodiment.

Mirrors with different reflectivity can also be placed under the glass substrate and configured to provide the backlighting. FIG. 7 is a block diagram of an AOI system optical module 700 that includes a mirror 903 for backside illumination, under an embodiment. The front side light source 804 provides light directed at the mirror 903, and light reflected from the mirror 903 provides the backlighting. The mirror 903 of an embodiment has a triangular configuration, but is not so limited. Each side of the triangular mirror 903 is coated with a film having a different reflectivity. The different reflectivities can be selected according to a substrate being imaged by positioning or rotating the triangular mirror to illuminate the substrate using light reflected from the appropriate side of the mirror. The light reflected from the substrate surface and mirror is directed to the TDI camera 206. The region housing the mirror under the substrate is much smaller than that required to house other light sources (e.g., LED, lamp, fiber optic illuminator, etc.). Alternative embodiments of the AOI system can use a mirror having any geometric configuration with any reflective film and/or other types and configurations of illuminators such as diffuse illuminators for example.

Figure 8:
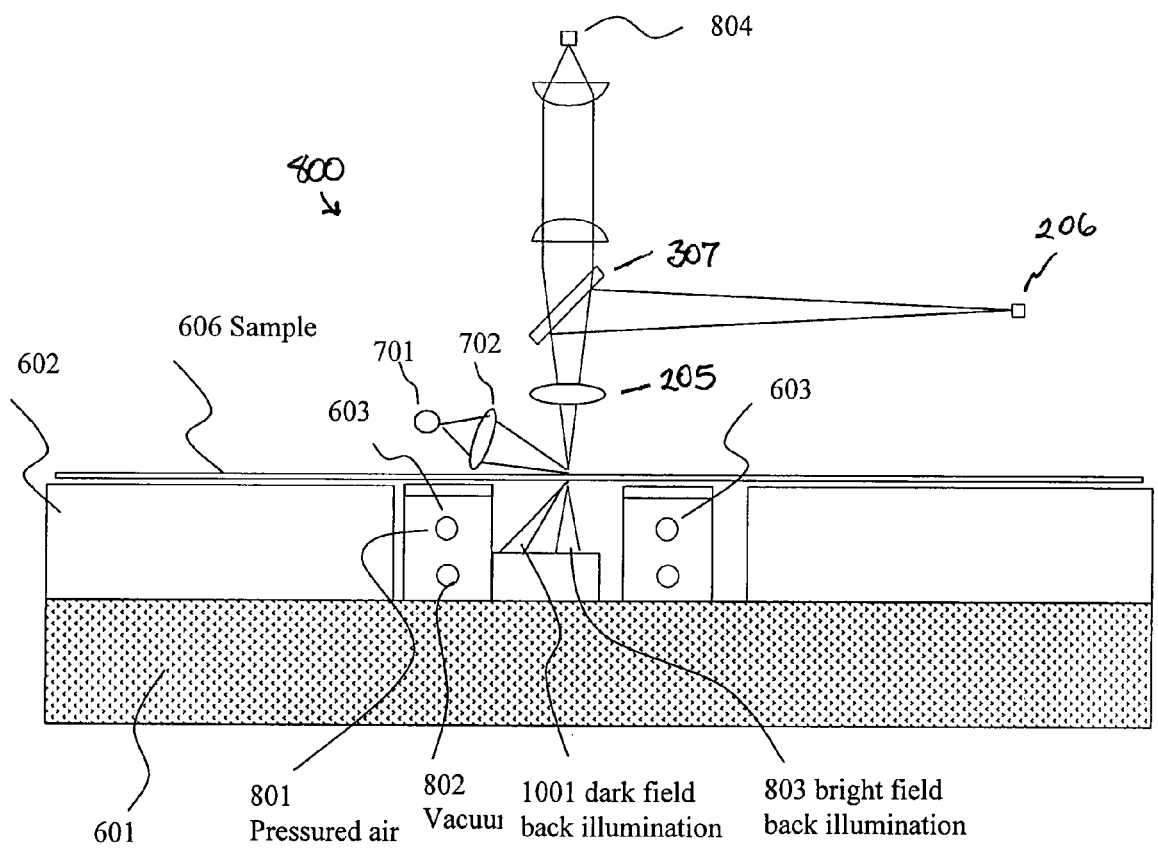
FIG. 8 is a block diagram of an AOI system optical module using front side lighting and backside lighting with bright field and dark field inspection, under an embodiment.

FIG. 8 is a block diagram of an AOI system optical module 800 using front side lighting and backside lighting with bright field and dark field inspection, under an embodiment. The AOI system 800 includes a front side light source 804 and a backside light source 803 for bright field inspection, as described above. The front side light source 804 and/or the back side light source 803 can be one or more of an LED, lamp, and fiber optic illuminator. The AOI system 800 also includes a front side light source 701 and a backside light source 1001 for dark field inspection, as described above. The dark field light source 1001 includes one or more of an LED, lamp, fiber illuminator, and laser source to name a few. The illumination area overlaps with the bright field illumination area. The configuration and operation of the optical module 800 relative to the front side light source with bright field and dark field inspection is as described above with reference to optical module 200 (FIG. 2) and optical module 500 (FIG. 5). The configuration and operation of the optical module 800 relative to the back side light source is as described above with reference to optical module 600 (FIG. 6) and optical module 700 (FIG. 7).

Regardless of lighting source type or configuration, many of which are described above, the LED intensity of LED sources should be held relatively constant during substrate inspection operations. While LED sources have a relatively long life, their intensity will drop due to LED or semiconductor aging effects. The AOI system of an embodiment uses a feedback system in conjunction with a standard sample to determine and compensate for any LED intensity drop. The LED intensity is measured regularly with the standard sample and, if the intensity varies (e.g., drops), the feed back system adjusts the LED current to provide the specification intensity of the AOI system.

Figure 9:
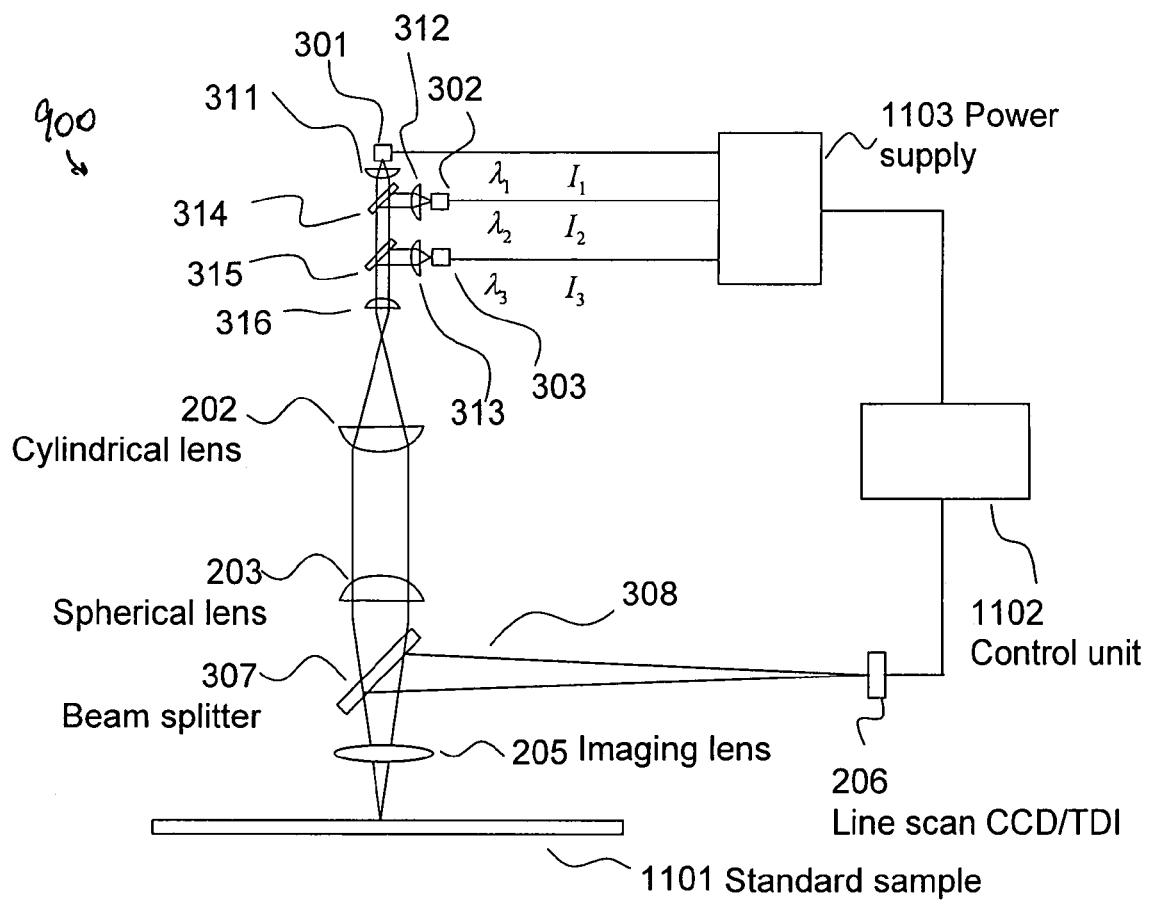
FIG. 9 is a block diagram of an AOI system optical module with a feedback system, under an embodiment.

FIG. 9 is a block diagram of an AOI system optical module 900 with a feedback system, under an embodiment. The optical module 900 described in this example includes the optical module 200 described above with reference to FIG. 2, but can include any optical module described herein. The optical module 900 includes a feedback system comprising a control unit 1102 coupled to an output of the TDI camera 206 and an input of a power supply 1103. Outputs of the power supply 1103 are coupled to the LED sources 301-301 so that the power supply controls current supplied to the LED sources.

In calibration operations, the optical module 900 uses a mirror 1101 as a reference substrate, and the light reflected from this mirror 1101 is used as a reference for the automatic calibration. The intensity of the light reflected back to the TDI camera 206 sensor from the mirror 1101 is measured and provided to the control unit 1102. If the reflected light reading is lower than a pre-specified value, the control unit generates a signal or command to control the power supply 1103 to increase the LED current until the measured light intensity reading at the TDI camera 206 returns to the pre-specified value.

The standard mirror can also be used for TDI camera calibration because the output of each TDI sensor pixel may not be the same when using a reference mirror 1101. The difference in pixel output can result from non-uniformity in the photo response of each pixel, the imaging lens, and the light sources. The first step of TDI calibration is to measure the output of each pixel of the TDI camera when receiving light reflected from the reference mirror 1101. Then that step is repeated but at a different level of the reflected light, achieved by either lowering the illumination light level or using another mirror of different reflectivity. The information of the measurements is used to determine two correction parameters, namely slope and offset, for each pixel or for groups of pixels. During actual substrate measurements, each pixel is subtracted by the offset and then multiplied by the slope for that pixel, thereby correcting for any non-uniformity.

Another feedback system can also be used to control the digital gain of the TDI camera 206 sensor in order to provide maximum dynamic range of the sensor. The feedback system controls or adjusts the TDI sensor maximum dynamic range by determining a first digital count at which the TDI sensor saturates, and determining a second digital count corresponding to the highest signal level in an image that is not saturated. The feedback system then sets and maintains the TDI digital gain to a value that is approximately equal to the first digital count divided by the second digital count, and this value provides the full dynamic range.

Figure 10:
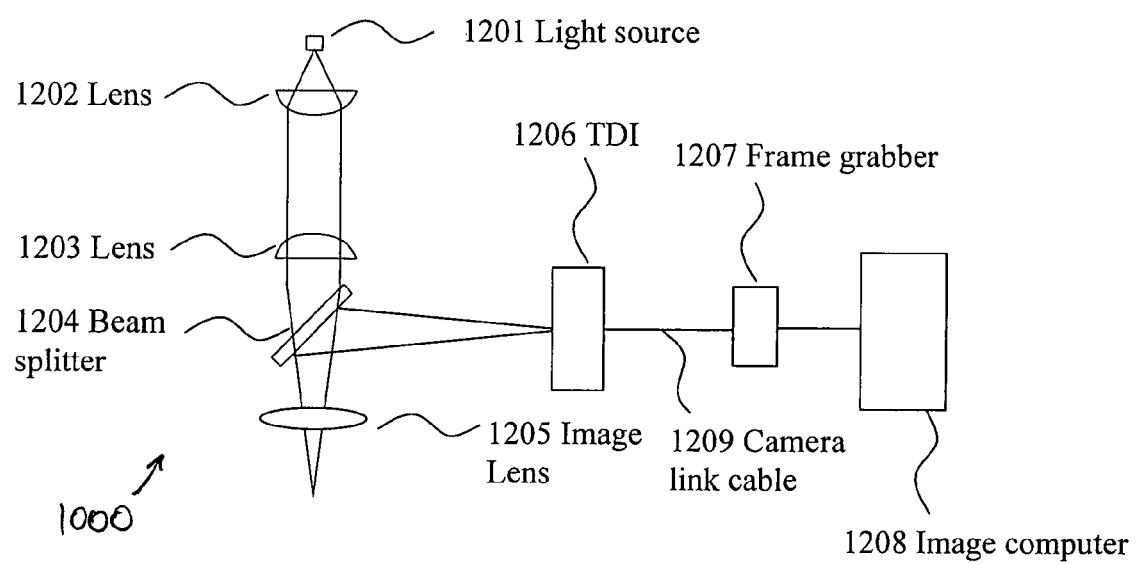
FIG. 10 is a modular AOI system, under an embodiment.

The AOI systems described herein are modular systems that enable reconfiguration or scalability as appropriate to substrates to be inspected or inspection operations. FIG. 10 is a module 1000, under an embodiment. The module 1000 comprises one or more components or combinations of components, for example, module including at least one light source 1201, two lenses 1202 and 1203 configured to direct light at a substrate, one beam splitter 1204 configured to reflect light from the substrate to a TDI camera, and imaging lens 1205 configured to focus an image of a portion of the substrate on the TDI camera 1206. A Camera Link cable or optical fiber 1209 is configured to transfer image data from the TDI camera 1206 to a frame grabber 1207. The frame grabber 1207 collects and analyzes image data and provides the image data to the image computer 1208. Each module 1000 is independent, and the number and/or type of modules included or installed on the system is flexible as appropriate to the substrate and the inspection procedures. As an example, FIG. 12 described below is an AOI system including three (3) optical modules 605, under an embodiment.

Figure 11:
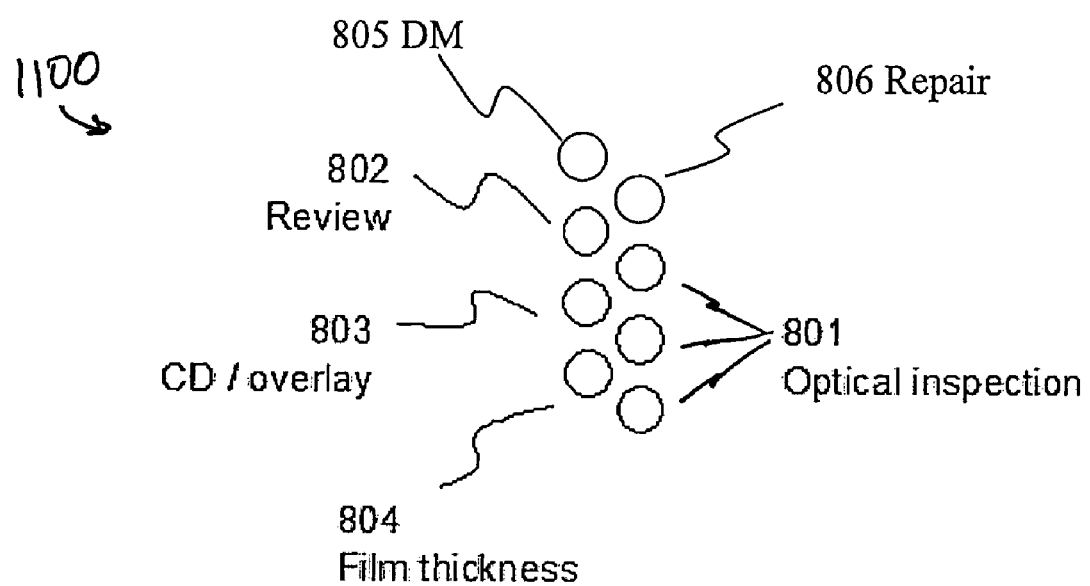
FIG. 11 shows a top view of an AOI system including a combination of optics modules with different inspection and metrology functions, under an embodiment.

FIG. 11 shows a top view of an AOI system 1100 including a combination of optics inspection modules 801 and review, repair, metrology modules 802-806, under an embodiment. The AOI system 1100 includes multiple (e.g., three (3)) optical inspection modules 801 combined with an optical review microscope 802, a critical dimension (CD) measurement and overlay accuracy measurement module 803, a thin film thickness measurement module 804, a digital macro measurement module and a repair module that uses laser cutting and CVD (or other similar technologies) to fix defects such as opens and shorts. The CD/overlay measurements require 50 nm or better accuracy. Any small amount of substrate vibration will make the accuracy data out of range. The air bearing vacuum chuck in the AOI system makes the CD/Overlay measurement available because it provides a down force to stabilize the glass during high-speed motion on air conveyor. As a result multiple functions can be performed using the AOI system 1100. Alternative embodiments can have different combinations and configurations of the modules described above.

The raw data generated by the TDI cameras of AOI systems are coupled to corresponding frame grabbers for processing, as described above. Conventional AOI systems use a Camera Link cable to couple the TDI camera to the frame grabber for data propagation. Camera Link is a data transmission protocol that requires special cable. Camera Link cables are subject to stringent requirements in the tightness of the twisted pairs of wires, shielding and length. In practical AOI applications, the cable length between the TDI camera (e.g., located on the rail above the stage) and the frame grabber (e.g., located inside the image computer) may run ten (10) meters or more, which requires repeaters to maintain signal integrity. Also, since Camera Link cables are bulky (about 15 mm in diameter), routing numerous such cables with flexible bending points for repeated bending becomes a very difficult task. Moreover, these electrical cables serve as antennas that often pick up interference signals and hence corrupt data signals.

The AOI system of an embodiment replaces the Camera Link cable between the TDI camera and the frame grabber with an optical fiber. Consequently, the AOI system converts the electrical signal output of the TDI camera to an optical signal and transmits the optical signal through one or more optical fibers. At the frame grabber, the optical signals are converted back to electrical signals. The optical fibers are thin, light weight and flexible and can link distant components without repeaters, so the frame grabber or other data processor can be located away from the AOI system. Furthermore, optical signals are immune to electrical interference and have higher bandwidths (hence allowing higher data rates) when compared to Camera Link cables.

Figure 12:
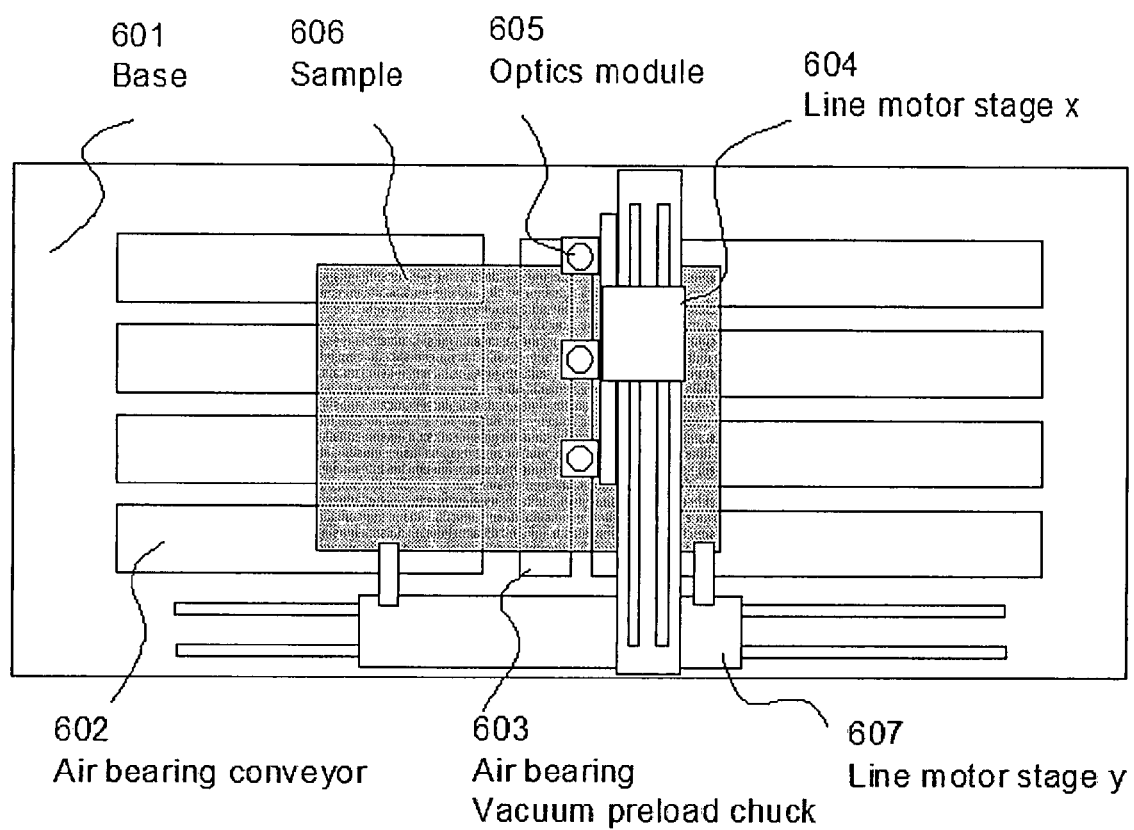
FIG. 12 is a block diagram of an AOI system for inspecting large substrates, under an embodiment.

FIG. 12 is a block diagram of an AOI system 1200 for inspecting large substrates, under an embodiment. The AOI system 1200 comprises a base 601 including an air bearing conveyer 602 and an air bearing vacuum preload chuck 603. The AOI system 1200 includes at least one optics module 605 (e.g., three (3) optics modules 605). The AOI system 1200 is configured to inspect large substrate including for example LCD glass substrates 606, but is not so limited. The optics module 605 includes illumination and imaging components that have been described above (e.g., optics module 200 in FIG. 2, optics module 500 in FIG. 5, optics module 600 in FIG. 6, optics module 700 in FIG. 7, optics module 800 in FIG. 8, and optics module 900 in FIG. 9).

During inspection operations, a one pixel wide line image of the substrate is generated by the TDI with each line trigger. The longer dimension of the line image area is placed parallel to the axis of the linear motor stage 604 (stage x) for optics motion. The glass substrate 606 moves in the direction parallel to the linear motor stage 607 (stage y), and is supported by the air bearing conveyor 602 and vacuum preload air bearing chuck 603. The vacuum preload of the air bearing chuck 603 provides rigidity and fly height control for the glass during motion on top of a thin layer of air. The linear motor stage 604 moves the optics module through the imaging area in steps until the entire glass is inspected.

Each time a substrate is loaded to the inspection system 1200, the substrate must be aligned with respect to the stage coordinates. Therefore, a high speed, high resolution, high accuracy and long travel distance actuator is needed to align the substrate. High speed substrate alignment enables high throughput (or short TACT time) and high productivity, while long travel distance tolerates larger loading errors. The high resolution, high accuracy actuator of the inspection system of an embodiment provides fine alignment of the substrate under the monitor of a microscope, thereby providing precise alignment, positioning, and registration.

Figure 13:
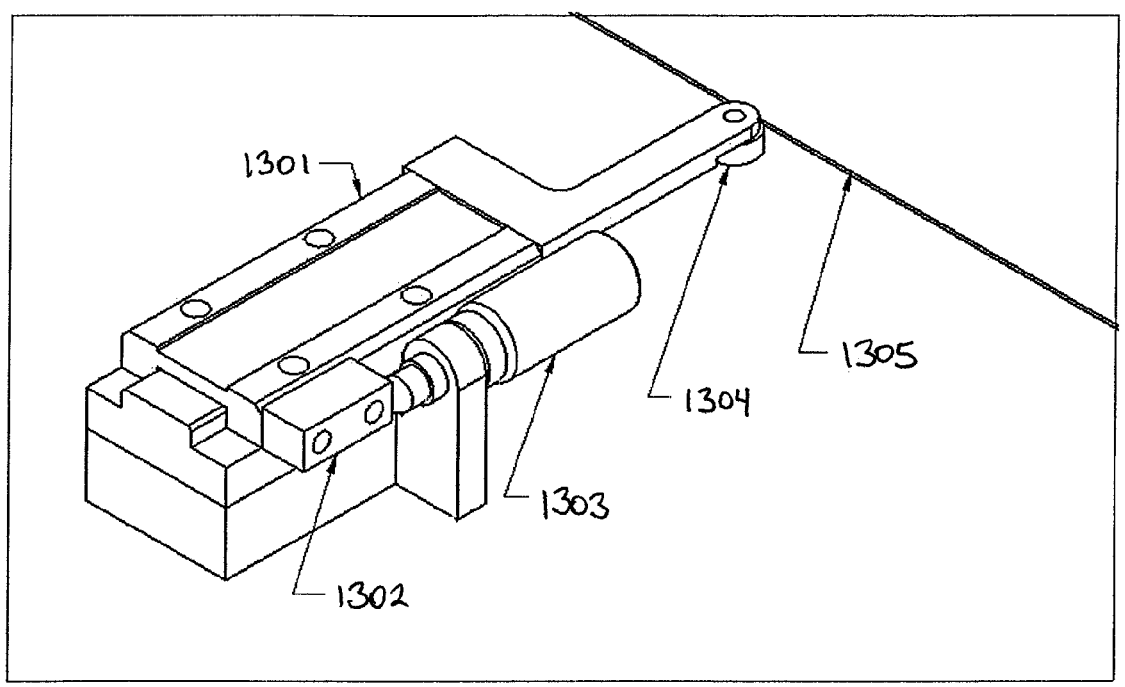
FIG. 13 shows the high-speed actuator of an inspection system, under an embodiment.

FIG. 13 shows the high-speed actuator of an inspection system, under an embodiment. The high speed actuator 1301 includes, but is not limited to, such devices as pneumatic actuators, voice coil actuators, linear motor actuators, and solenoids. The high speed actuator 1301 includes an aligner pin 1304 that defines the alignment or positioning of the substrate 1305. The substrate can be spring loaded or gravity loaded toward the aligner pin 1304. The aligner pin 1304 is in contact with the substrate 1305 and is driven by the high speed actuator 1301. The hard stop 1302 of the aligner pin 1304 is controlled by the high resolution actuator 1303. The actuation force from the high speed actuator 1301 is less than the force exerted in the opposite direction by the high resolution actuator 1303. The hard stop position 1302, which is controlled by the high resolution actuator 1303, determines the final position or alignment accuracy and resolution of the aligner pin 1304.

The inspection systems and methods of an embodiment include a system comprising an illumination component. The system of an embodiment includes a lens array configured to direct illumination of the illumination component at a portion of a substrate. The lens array of an embodiment includes at least one Fresnel lens. The system of an embodiment includes a camera positioned to receive reflected light resulting from an interaction of the illumination with a surface of the substrate. The camera of an embodiment includes a time delay integration (TDI) sensor.

The illumination component of an embodiment comprises a plurality of LED light sources. Each LED light source of an embodiment emits light at a different wavelength. The system of an embodiment includes a controller coupled to the plurality of LED light sources and configured to independently control each of the LED light sources.

The system of an embodiment includes a beam splitter positioned between the lens array and the substrate. The beam splitter of an embodiment is a dichroic beam splitter.

The system of an embodiment includes an imaging lens positioned between the beam splitter and the substrate. The imaging lens of an embodiment is a telecentric lens.

The lens array of an embodiment comprises a plurality of Fresnel lenses.

The illumination component of an embodiment includes a bright field light source and a dark field light source. The bright field light source of an embodiment includes a first front side lighting source at a first side of the substrate. The bright field light source of an embodiment includes a first back side lighting source at a second side of the substrate. The second side of the substrate of an embodiment is opposite to the first side. The first back side lighting source of an embodiment is a mirror configured to reflect the illumination of the illumination component.

The dark field light source of an embodiment includes a second front side lighting source at a first side of the substrate. The dark field light source of an embodiment includes a second back side lighting source at a second side of the substrate, wherein the second side is opposite the first side.

The system of an embodiment includes a feedback system coupled to an output of the camera. The feedback system of an embodiment is configured to control the illumination component. The feedback system of an embodiment is configured to control a gain of the camera.

The system of an embodiment includes a frame grabber. The system of an embodiment includes an optical fiber coupled to the camera and the frame grabber.

The system of an embodiment includes an air bearing conveyor configured to transport the substrate. The system of an embodiment includes a moving mechanism to cause a relative movement of the substrate.

The system of an embodiment includes a vacuum preload air bearing chuck configured to support and stabilize the substrate.

The system of an embodiment includes a high speed, high resolution, high accuracy and long travel distance actuator.

The camera of an embodiment includes a line scan charge-coupled device (CCD).

The camera of an embodiment includes an intensified CCD device.

The camera of an embodiment includes a photomultiplier tube (PMT) array.

The camera of an embodiment includes a complementary metal-oxide-semiconductor (CMOS) detector.

The illumination component of an embodiment comprises an LED light source. The LED light source of an embodiment emits light at a plurality of wavelengths.

The substrate of an embodiment includes a liquid crystal display (LCD).

The substrate of an embodiment includes a flat panel display (FPD).

The substrate of an embodiment includes an organic light emitting diode (OLED) substrate.

The substrate of an embodiment includes a mask.

The substrate of an embodiment includes a semiconductor wafer.

The inspection systems and methods of an embodiment include a system comprising an illumination component. The system of an embodiment includes a lens array configured to direct illumination of the illumination component at a portion of a substrate. The lens array of an embodiment includes at least one Fresnel lens. The system of an embodiment includes an imaging lens positioned between the lens array and the substrate. The imaging lens of an embodiment is a telecentric lens.

The system of an embodiment includes a camera positioned to receive reflected light resulting from an interaction of the illumination with a surface of the substrate. The camera of an embodiment includes a time delay integration sensor. The camera of an embodiment includes a line scan CCD. The camera of an embodiment includes an ICCD. The camera of an embodiment includes a PMT array. The camera of an embodiment includes a CMOS detector.

The illumination component of an embodiment comprises a controller coupled to a plurality of LED light sources. Each LED light source of an embodiment emits light at a different wavelength. The controller of an embodiment is configured to independently control each of the LED light sources.

The illumination component of an embodiment includes a bright field light source and a dark field light source. The illumination component of an embodiment includes one or more of at least one front side lighting source and at least one back side lighting source. The at least one back side lighting source of an embodiment includes a mirror configured to reflect the illumination of the illumination component.

The system of an embodiment includes a feedback system coupled to an output of the camera. The feedback system of an embodiment is configured to control one or more of the illumination component, and a gain of the camera.

The system of an embodiment includes an optical fiber coupled to the camera and at least one image processor.

The system of an embodiment includes a conveyor configured to transport the substrate.

The system of an embodiment includes a high speed, high resolution, high accuracy and long travel distance actuator.

The illumination component of an embodiment comprises an LED light source. The LED light source of an embodiment emits light at a plurality of wavelengths.

The inspection systems and methods of an embodiment include a method comprising generating illumination. The method of an embodiment includes directing the illumination at a portion of a substrate using a Fresnel lens. The method of an embodiment includes receiving at a time delay integration (TDI) sensor reflected light resulting from an interaction of the illumination with a surface of the substrate. The method of an embodiment includes generating an image of the substrate using information of the reflected light.

The method of an embodiment includes directing the reflected light at the TDI sensor using an imaging lens. The imaging lens of an embodiment includes a telecentric lens.

Generating illumination under the method of an embodiment comprises generating light having a plurality of wavelengths.

The method of an embodiment includes independently controlling a plurality of light sources corresponding to the plurality of wavelengths.

Generating illumination under the method of an embodiment comprises generating bright field illumination and dark field illumination.

Generating illumination under the method of an embodiment comprises generating one or more front side illumination and back side illumination. Generating the back side illumination under the method of an embodiment comprises generating a reflection of the front side illumination.

The method of an embodiment includes generating an optical signal of the image from an electrical signal of the image. The method of an embodiment includes transferring the optical signal.

The method of an embodiment includes detecting a defect in the substrate using data of the image.

The inspection systems and methods of an embodiment include a method comprising generating illumination. The method of an embodiment includes directing the illumination towards a substrate using a Fresnel lens. The method of an embodiment includes directing reflected light at an imaging sensor using an imaging lens. The reflected light of an embodiment results from an interaction of the illumination with a surface of the substrate. The imaging lens of an embodiment includes a telecentric lens. The method of an embodiment includes generating an image of the substrate using the reflected light.

The method of an embodiment includes detecting a defect in the substrate using the image.

The imaging sensor under the method of an embodiment includes a time delay integration (TDI) sensor.

The imaging sensor under the method of an embodiment includes a line scan CCD.

The imaging sensor under the method of an embodiment includes an ICCD.

The imaging sensor under the method of an embodiment includes a PMT array.

The imaging sensor under the method of an embodiment includes a CMOS detector.

Aspects of the inspection systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the inspection systems and methods include microcontrollers with memory (such as electronically erasable programmable read-only memory (EEPROM)), embedded microprocessors, firmware, software, etc. Furthermore, aspects of the inspection systems and methods may be embodied in microprocessors having software-based circuit emulation, discrete logic (sequential and combinatorial), custom devices, fuzzy logic (in neural networks), quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that components of the various inspection systems and methods disclosed herein may be described using computer aided design tools and expressed (or represented) as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over couplings or connections via one or more data transfer protocols (e.g., HTTP, FTP, SMTP, etc.). The couplings or connections supporting the transfers described above include wired couplings, wireless couplings, and hybrid wired/wireless couplings, but are not so limited. Furthermore, the couplings can include various networks and/or network components (not shown) of a communication service provider or carrier, but are not so limited. The network and corresponding network components, when present in the couplings, can be any of a number of network types known in the art including, but not limited to, local area networks (LANs), metropolitan area networks (MANs), wide area networks (WANs), proprietary networks, backend networks, and the Internet. When received within a computer system via one or more computer-readable media, such data and/or instruction-based expressions of the above described systems and methods may be processed by a processing entity (e.g., one or more processors) within the computer system in conjunction with execution of one or more other computer programs.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the inspection systems and methods is not intended to be exhaustive or to limit the systems and methods described to the precise form disclosed. While specific embodiments of, and examples for, the inspection systems and methods are described herein for illustrative purposes, various equivalent modifications are possible within the scope of other inspection systems and methods, as those skilled in the relevant art will recognize. The teachings of the inspection systems and methods provided herein can be applied to other processing systems and methods, not only for the inspection systems and methods described above.

The elements and acts of the various embodiments described above can be combined to provide further embodiments. These and other changes can be made to the inspection systems and methods in light of the above detailed description.

In general, in the following claims, the terms used should not be construed to limit the inspection systems and methods to the specific embodiments disclosed in the specification and the claims, but should be construed to include all systems that operate under the claims. Accordingly, the inspection systems and methods are not limited by the disclosure, but instead the scope of the inspection systems and methods is to be determined entirely by the claims.

While certain aspects of the inspection systems and methods are presented below in certain claim forms, the inventors contemplate the various aspects of the inspection systems and methods in any number of claim forms. Accordingly, the inventors reserve the right to add additional claims after filing the application to pursue such additional claim forms for other aspects of the inspection systems and methods.

What is claimed is:

1. A system comprising:
an illumination component;
a lens array configured to direct illumination of the illumination component at a portion of a substrate, wherein the lens array includes at least one Fresnel lens;
an imaging lens positioned between said lens array and said substrate, wherein the imaging lens is a telecentric lens; and
a camera positioned to receive reflected light resulting from an interaction of the illumination with a surface of the substrate, wherein the camera includes a time delay integration (TDI) sensor.

2. The system of claim 1, wherein the illumination component comprises a plurality of LED light sources, wherein each LED light source emits light at a different wavelength.

3. The system of claim 2, comprising a controller coupled to the plurality of LED light sources and configured to independently control each of the LED light sources.

4. The system of claim 1, comprising a beam splitter positioned between the lens array and the substrate, wherein the beam splitter is a dichroic beam splitter.

5. The system of claim 4, comprising an imaging lens positioned between the beam splitter and the substrate, wherein the imaging lens is a telecentric lens.

6. The system of claim 1, wherein the lens array comprises a plurality of Fresnel lenses.

7. The system of claim 1, wherein the illumination component includes a bright field light source and a dark field light source.

8. The system of claim 7, wherein the bright field light source includes a first front side lighting source at a first side of the substrate.

9. The system of claim 8, wherein the bright field light source includes a first back side lighting source at a second side of the substrate, wherein the second side is opposite to the first side.

10. The system of claim 9, wherein the first back side lighting source is a mirror configured to reflect the illumination of the illumination component.

11. The system of claim 7, wherein the dark field light source includes a second front side lighting source at a first side of the substrate.

12. The system of claim 11, wherein the dark field light source includes a second back side lighting source at a second side of the substrate, wherein the second side is opposite the first side.

13. The system of claim 1, comprising a feedback system coupled to an output of the camera.

14. The system of claim 13, wherein the feedback system is configured to control the illumination component.

15. The system of claim 13, wherein the feedback system is configured to control a gain of the camera.

16. The system of claim 1, comprising:
a frame grabber; and
an optical fiber coupled to the camera and the frame grabber.

17. The system of claim 1, comprising:
an air bearing conveyor configured to transport the substrate; and
a moving mechanism to cause a relative movement of the substrate.

18. The system of claim 17, comprising a vacuum preload air bearing chuck configured to support and stabilize the substrate.

19. The system of claim 1, comprising a high speed, high resolution, high accuracy and long travel distance actuator.

20. The system of claim 1, wherein the camera includes one or more or a line scan charge-coupled device (CCD), intensified CCD device, photomultiplier tube (PMT) array, and complementary metal-oxide-semiconductor (CMOS) detector.

21. The system of claim 1, wherein the illumination component comprises an LED light source, wherein the LED light source emits light at a plurality of wavelengths.

22. The system of claim 1, wherein the substrate includes one or more of a liquid crystal display (LCD), a flat panel display (FPD), an organic light emitting diode (OLED) substrate, a mask, and a semiconductor wafer.

23. A system comprising:
an illumination component;
a lens array configured to direct illumination of the illumination component at a portion of a substrate, wherein the lens array includes at least one Fresnel lens; and
an imaging lens positioned between the lens array and the substrate, wherein the imaging lens is a telecentric lens.

24. The system of claim 23, comprising a camera positioned to receive reflected light resulting from an interaction of the illumination with a surface of the substrate, wherein the camera includes one or more of a time delay integration sensor, line scan CCD, ICCD, PMT array, and CMOS detector.

25. The system of claim 23, wherein the illumination component comprises a controller coupled to a plurality of LED light sources, wherein each LED light source emits light at a different wavelength, wherein the controller is configured to independently control each of the LED light sources.

26. The system of claim 23, wherein the illumination component includes a bright field light source and a dark field light source.

27. The system of claim 26, wherein the illumination component includes one or more of at least one front side lighting source and at least one back side lighting source.

28. The system of claim 27, wherein the at least one back side lighting source includes a mirror configured to reflect the illumination of the illumination component.

29. The system of claim 23, comprising a feedback system coupled to an output of the camera, wherein the feedback system is configured to control one or more of the illumination component, and a gain of the camera.

30. The system of claim 23, comprising an optical fiber coupled to the camera and at least one image processor.

31. The system of claim 23, comprising a conveyor configured to transport the substrate.

32. The system of claim 23, comprising a high speed, high resolution, high accuracy and long travel distance actuator.

33. The system of claim 23, wherein the illumination component comprises an LED light source, wherein the LED light source emits light at a plurality of wavelengths.

34. A method comprising:
generating illumination;
directing the illumination at a portion of a substrate using a Fresnel lens;
positioning an imaging lens between said Fresnel lens and said substrate,
wherein said imaging lens is a telecentric lens;
receiving at a time delay integration (TDI) sensor reflected light resulting from an interaction of the illumination with a surface of the substrate; and
generating an image of the substrate using information of the reflected light.

35. The method of claim 34, wherein generating illumination comprises generating light having a plurality of wavelengths.

36. The method of claim 35, comprising independently controlling a plurality of light sources corresponding to the plurality of wavelengths.

37. The method of claim 34, wherein generating illumination comprises generating bright field illumination and dark field illumination.

38. The method of claim 34, wherein generating illumination comprises generating one or more front side illumination and back side illumination.

39. The method of claim 38, wherein generating the back side illumination comprises generating a reflection of the front side illumination.

40. The method of claim 34, comprising:
generating an optical signal of the image from an electrical signal of the image; and
transferring the optical signal.

41. The method of claim 34, comprising detecting a defect in the substrate using data of the image.

42. A method comprising:
generating illumination;
directing the illumination towards a substrate using a Fresnel lens;
directing reflected light at an imaging sensor using an imaging lens, wherein the reflected light results from an interaction of the illumination with a surface of the substrate, wherein the imaging lens is a telecentric lens located between said Fresnel lens and said substrate; and
generating an image of the substrate using the reflected light.

43. The method of claim 42, comprising detecting a defect in the substrate using the image.

44. The method of claim 42, wherein the imaging sensor includes one or more of a time delay integration (TDI) sensor, line scan CCD, ICCD, PMT array, and CMOS detector.

* * * * *